United States Patent
Moriya

(10) Patent No.: US 6,236,056 B1
(45) Date of Patent: May 22, 2001

(54) DEFECT EVALUATION APPARATUS FOR EVALUATING DEFECTS AND SHAPE INFORMATION THEREOF IN AN OBJECT OR ON THE SURFACE OF AN OBJECT

(75) Inventor: Kazuo Moriya, Ageo (JP)

(73) Assignee: Mitsui Mining & Smelting Co., Ltd. (JP)

( * ) Notice: Subject to any disclaimer, the term of this patent is extended or adjusted under 35 U.S.C. 154(b) by 0 days.

(21) Appl. No.: 09/161,943

(22) Filed: Sep. 28, 1998

(30) Foreign Application Priority Data

Sep. 30, 1997 (JP) .................................................. 9-266466

(51) Int. Cl.[7] .................................................. G01N 21/86
(52) U.S. Cl. .................................. 250/559.4; 250/559.45
(58) Field of Search ........................... 250/559.4, 559.45, 250/559.22; 356/237.2–237.5

(56) References Cited

U.S. PATENT DOCUMENTS

| 4,614,427 | 9/1986 | Koizumi et al. . |
| 4,893,932 | 1/1990 | Knollenberg . |
| 4,966,457 | * 10/1990 | Hayano et al. ...................... 356/237 |
| 5,032,734 | 7/1991 | Orazio, Jr. et al. . |
| 5,424,536 | 6/1995 | Moriya . |
| 5,426,506 | 6/1995 | Ellingson et al. . |

* cited by examiner

Primary Examiner—Que T. Le
(74) Attorney, Agent, or Firm—Cook, Alex, McFarron, Manzo, Cummings & Mehler, Ltd.

(57) ABSTRACT

A defect evaluation apparatus of this invention includes a laser irradiation unit for obliquely irradiating a laser beam onto an object, and an observation unit for observing scattered light from inside the object or a surface of the object. The laser irradiation unit irradiates the laser beam onto the object from a plurality of incident directions around an observation optical axis, and the observation unit receives the scattered light from the object to obtain shape information of a defect in the object or on the surface of the object.

9 Claims, 5 Drawing Sheets

DEFECT EVALUATION APPARATUS FOR EVALUATING DEFECTS AND SHAPE INFORMATION THEREOF IN AN OBJECT OR ON THE SURFACE OF AN OBJECT

BACKGROUND OF THE INVENTION

1. Field of the Invention

The present invention relates to an apparatus for evaluating a defect or the like on, e.g., a semiconductor wafer. A defect means a defect, a foreign substance, a flaw, a particle, or unevenness.

2. Related Background Art

In a conventional apparatus for evaluating a defect in an object such as a semiconductor wafer, a laser beam is irradiated on the object obliquely with respect to the surface of an object to observe scattered light from a defect inside the object is observed from the object surface side in a direction different from the laser beam incident direction, thereby detecting a defect or a particle in the object (Japanese Patent Application Laid-Open No. 4-24541). In this apparatus, the scattered light is observed in a direction different from the direction of the laser beam reflected by the object, thereby minimizing the influence of reflected light. Also, the wavelength of laser beam or the object temperature can be changed to adjust the depth in the object to which the laser beam travels.

In this apparatus, however, when a defect near the surface of the object is observed, a flaw or the like on the surface is observed together in the same observation field. Since the defect cannot be discriminated from the flaw, accurate evaluation cannot be obtained.

To solve this problem, in a conventional defect evaluation apparatus comprising a laser irradiation means for obliquely irradiating a laser beam onto the observation surface of an object, and an observation means for observing, through the observation surface, scattered light which is generated by a defect or a particle in the object when refracted light of the laser beam becomes incident thereon, a component discrimination means is used to allow observation with both light mainly containing a p-polarized light component and light mainly containing an s-polarized light component. With this apparatus, even when a defect near the surface of the object surface is to be observed, and a flaw or the like on the surface is present in the same observation field, the defect can be discriminated from the flaw, so accurate evaluation can be obtained.

However, the shape information of the defect cannot be obtained.

SUMMARY OF THE INVENTION

It is an object of the present invention to provide a defect evaluation apparatus capable of separating defects or the like of an object into defects in the object and those on the object surface, and simultaneously obtaining the shape information of the defect.

In order to achieve the above object, according to the present invention, there is provided a defect evaluation apparatus comprising laser irradiation means for obliquely irradiating a laser beam onto an object, and observation means for observing scattered light from inside the object or a surface of the object, wherein the laser irradiation means irradiates the laser beam onto the object from a plurality of incident directions around an observation optical axis, and the observation means receives the scattered light from the object to obtain shape information of a defect or the like in the object or on the surface of the object.

DETAILED DESCRIPTION OF THE PREFERRED EMBODIMENTS

Figure 1:
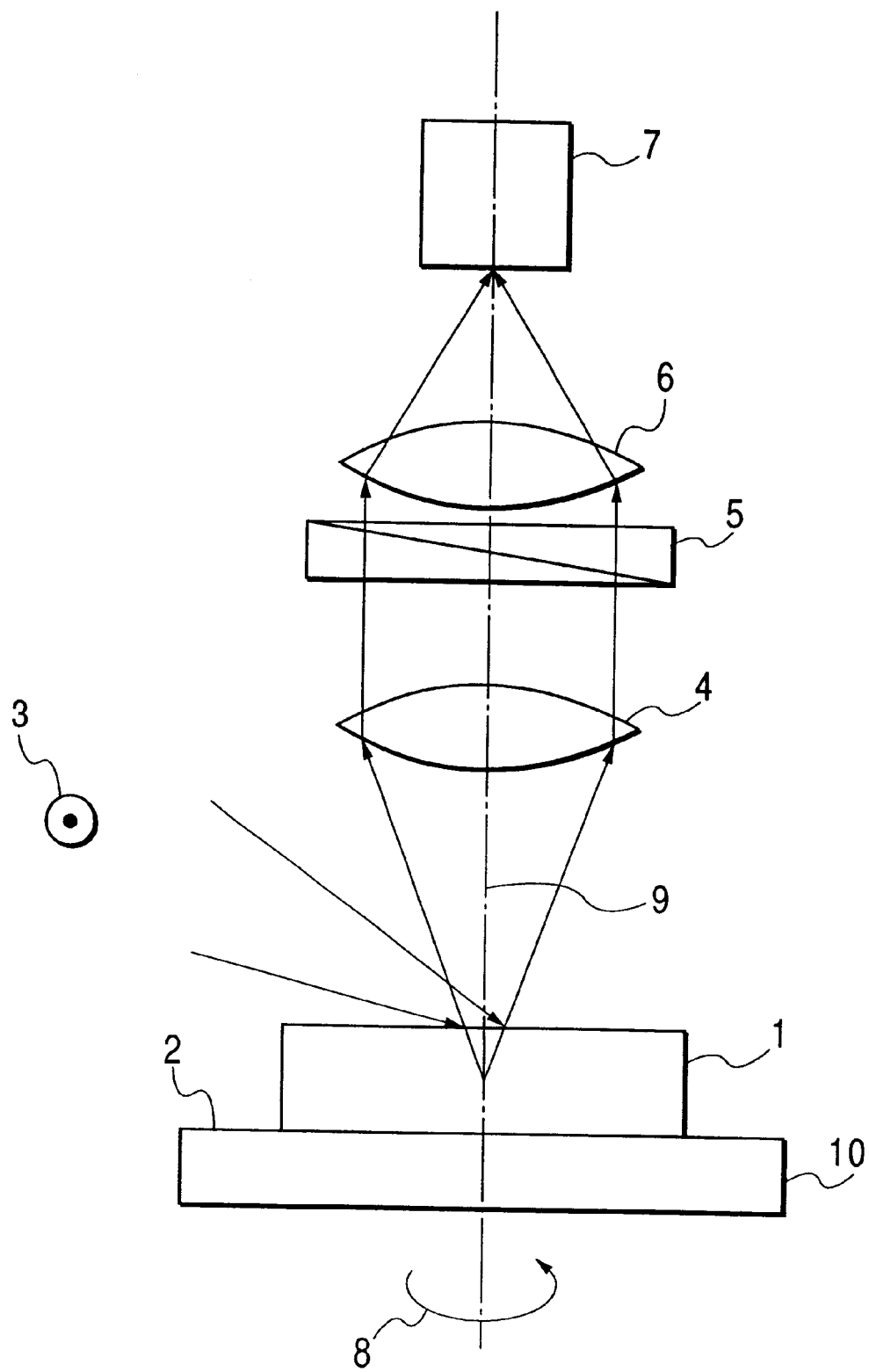
FIG. 1 is a view showing the arrangement of the first embodiment.

FIG. 1 is a view showing the arrangement of the first embodiment.

This apparatus comprises a laser irradiation unit (not shown) for obliquely irradiating a laser beam onto an observation surface 2 of an object 1, a polarizer (not shown) for polarizing the laser beam to irradiate light 3 containing an s-polarized light component onto the object, an objective lens 4 for observing scattered light generated by unevenness on the observation surface 2 of the object 1 upon incidence of the laser beam, a polarizer 5 for polarizing the scattered light from the object 1 to extract an s-polarized light component, an imaging lens 6, a light-receiving element 7, and a rotating mechanism 8 for rotating the object to change the incident direction of the laser beam on the object 1. The rotating mechanism 8 comprises a stage 10 capable of rotating the object 1 about an observation optical axis 9. The incident direction of the laser beam on the object 1 can be arbitrarily selected by rotating the stage 10. The object 1 can also be moved on the plane of the stage 10 such that the entire surface of the object 1 can be measured.

To suppress the influence of dependence of the incident laser beam on azimuth due to poor mechanical accuracy of the rotating mechanism (including the flatness of the stage), the number of incident directions is preferably as large as possible. In this embodiment, the laser beam irradiating on the object is a parallel beam. However, a condensed beam may be used. In addition, Wollaston prisms may be used in place of the polarizers.

In this arrangement, the laser beam containing various polarized light components is polarized to obtain light 3 containing an s-polarized light component by the polarizer, and the light 3 is irradiated on the observation surface 2. Since the irradiated laser beam is an s-polarized light component, the incident light is mostly reflected by the observation surface 2 and rarely transmitted through the observation surface 2. The incident angle is set such that the direction of the light reflected by the object does not coincide with the observation optical axis 9. With this arrangement, the incident light generates scattered light on unevenness on the observation surface 2 of the object 1, and the scattered light is observed.

In this embodiment, the laser beam is irradiated from a plurality of directions by rotating the object. Instead, the object may be fixed while the laser beam irradiation means is rotated about the observation optical axis. In this case, a means for rotating the polarizer 5 in accordance with rotation of the laser irradiation means is provided.

In this embodiment, an epitaxial film is used as the object.

Figure 2:
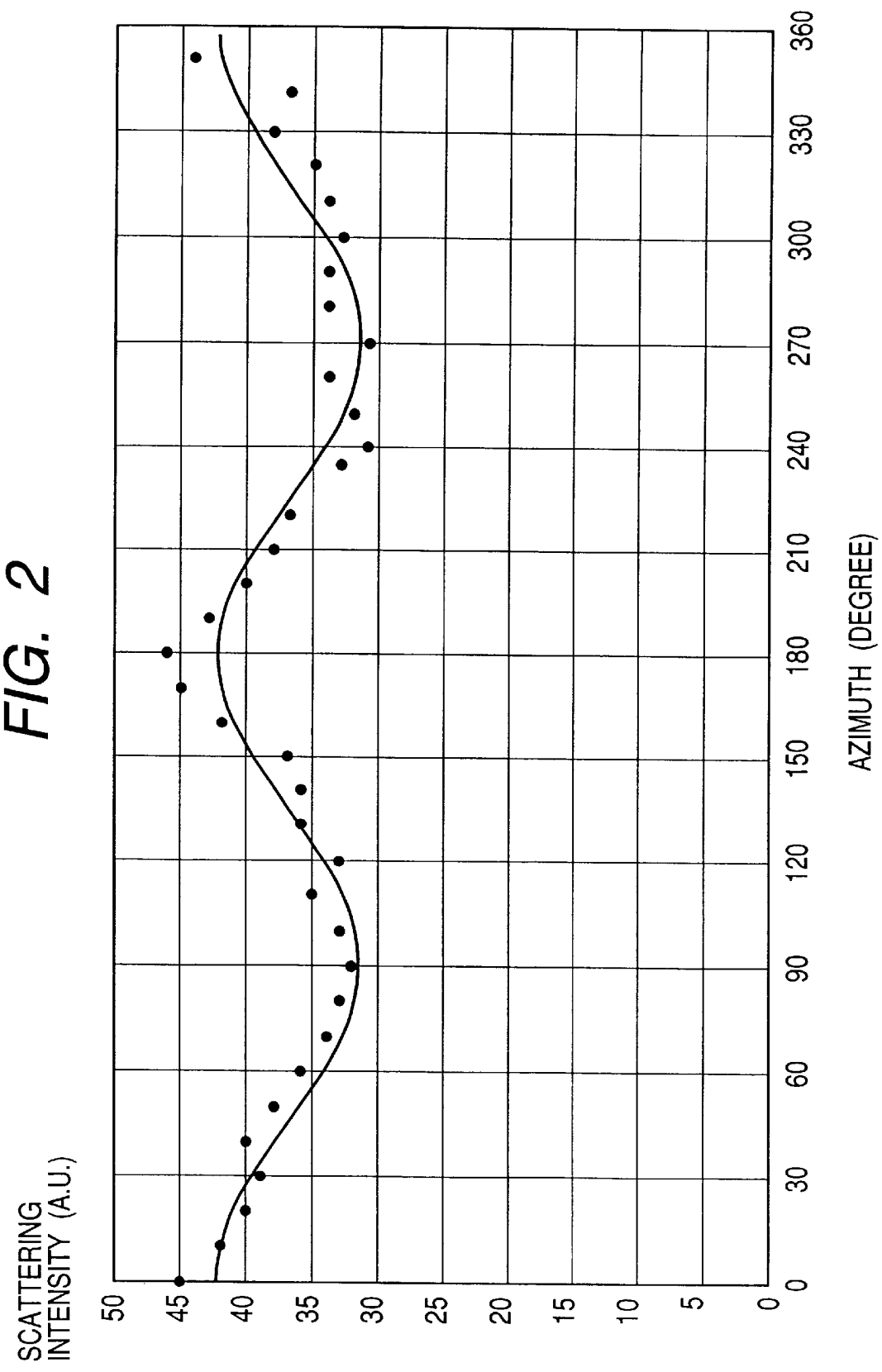
FIG. 2 is a graph which plots the scattering intensity from an epitaxial film as a function of the laser beam incident direction, i.e., azimuth in the apparatus of the first embodiment.

FIG. 2 is a graph which plots the scattering intensity from the epitaxial film as a function of the laser beam incident direction, i.e., azimuth in the apparatus of the first embodiment.

The curve indicates the scattering intensity of the scattered light from the epitaxial film in irradiating s-polarized laser beam on the epitaxial film.

The presence of a flaw or the like on the film surface can be estimated from the scattering intensity of the observed scattered light. More specifically, since the scattering intensity changes at a 180° period, i.e., twice per rotation, the shape can be estimated to be linear.

Figure 3:
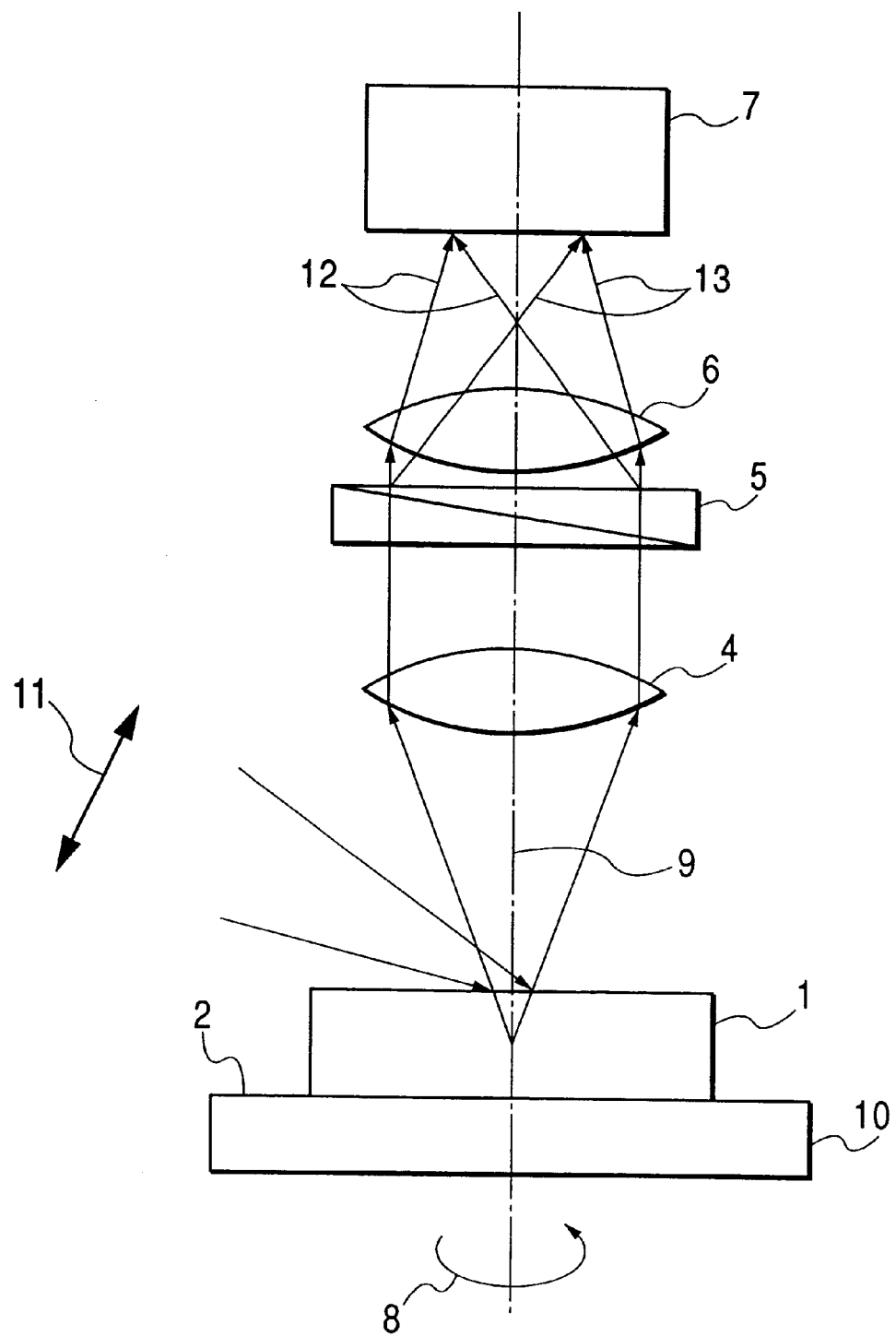
FIG. 3 is a view showing the arrangement of the second embodiment.

FIG. 3 is a view showing the arrangement of the second embodiment.

This apparatus comprises a laser irradiation unit (not shown) for obliquely irradiating a laser beam onto the observation surface of an object, a polarizer (not shown) for polarizing the laser beam to irradiate light 11 containing a p-polarized light component onto the object, an objective lens 4 for observing scattered light generated by a defect in the object or on the surface of the object upon incidence of the laser beam, a polarizer 5 for polarizing the scattered light from an object 1 to extract a p-polarized light component 12 or an s-polarized light component 13, an imaging lens 6, a light-receiving element 7, and a rotating mechanism 8 for rotating the object 1 to change the incident direction of the laser beam on the object. The rotating mechanism 8 comprises a stage 10 capable of rotating the object about an observation optical axis 9. The incident direction of the laser beam on the object 1 can be arbitrarily selected by rotating the stage. The object 1 can also be moved on the plane of the stage 10 such that the entire surface of the object 1 can be measured. The incident angle is set such that the direction of the light reflected by the object 1 does not coincide with the observation optical axis 9.

To suppress the influence of dependence of the incident laser beam on azimuth due to poor mechanical accuracy of the rotating mechanism (including flatness of the stage), the number of incident directions is preferably as large as possible. In this embodiment, the laser beam to be irradiated on the object is a parallel beam. However, a condensed beam may be used. In addition, Wollaston prisms may be used in place of the polarizers.

In this arrangement, the laser beam containing various polarized light components is polarized to obtain light 11 containing a p-polarized light component by the polarizer, and the light 11 is irradiated on the observation surface 2. Since the irradiated laser beam is a p-polarized light component, the incident light is transmitted through the observation surface 2 almost without being influenced by scattering due to unevenness on the observation surface 2, and becomes refracted light. Especially, when the incident angle (the angle formed by the laser beam incident direction and the observation optical axis) equals to a Brewster angle, all the p-polarized light component is transmitted. However, if the incident angle does not equal to a Brewster angle, reflection due to unevenness on the observation surface 2 also exists, so the scattered light from the observation surface 2 contains not only a p-polarized light component but also an s-polarized light component. In this embodiment, not only the p-polarized light component 12 but also the s-polarized light component 13 can be extracted by the polarizer. For this reason, a defect on the surface can be easily discriminated from a defect in the object on the basis of the component ratio. The incident angle is set such that the direction of the light reflected by the object 1 does not coincide with the observation optical axis 9. Therefore, the laser beam generates scattered light by a defect in the object or on the surface of the object or the like, and the scattered light is observed.

In this embodiment, the laser beam is irradiated from a plurality of directions by rotating the object. Instead, the object may be fixed while the laser beam irradiation means is rotated about the observation optical axis. In this case, a means for rotating the polarizer between the objective lens and the imaging lens in accordance with rotation of the laser irradiation means is provided.

According to the second embodiment, defects in the object can be separated from those on the surface. In addition, as in the first embodiment, the shape information of a defect in the object or on the surface of the object or the like can be obtained.

In this embodiment, when the scattering intensity from the object was plotted with respect to the laser beam incident direction, i.e., azimuth, the scattering intensity changed at a 90° period, i.e., four times per rotation. This perhaps suggests the presence of an internal defect having a regular octahedral shape.

Figure 4:
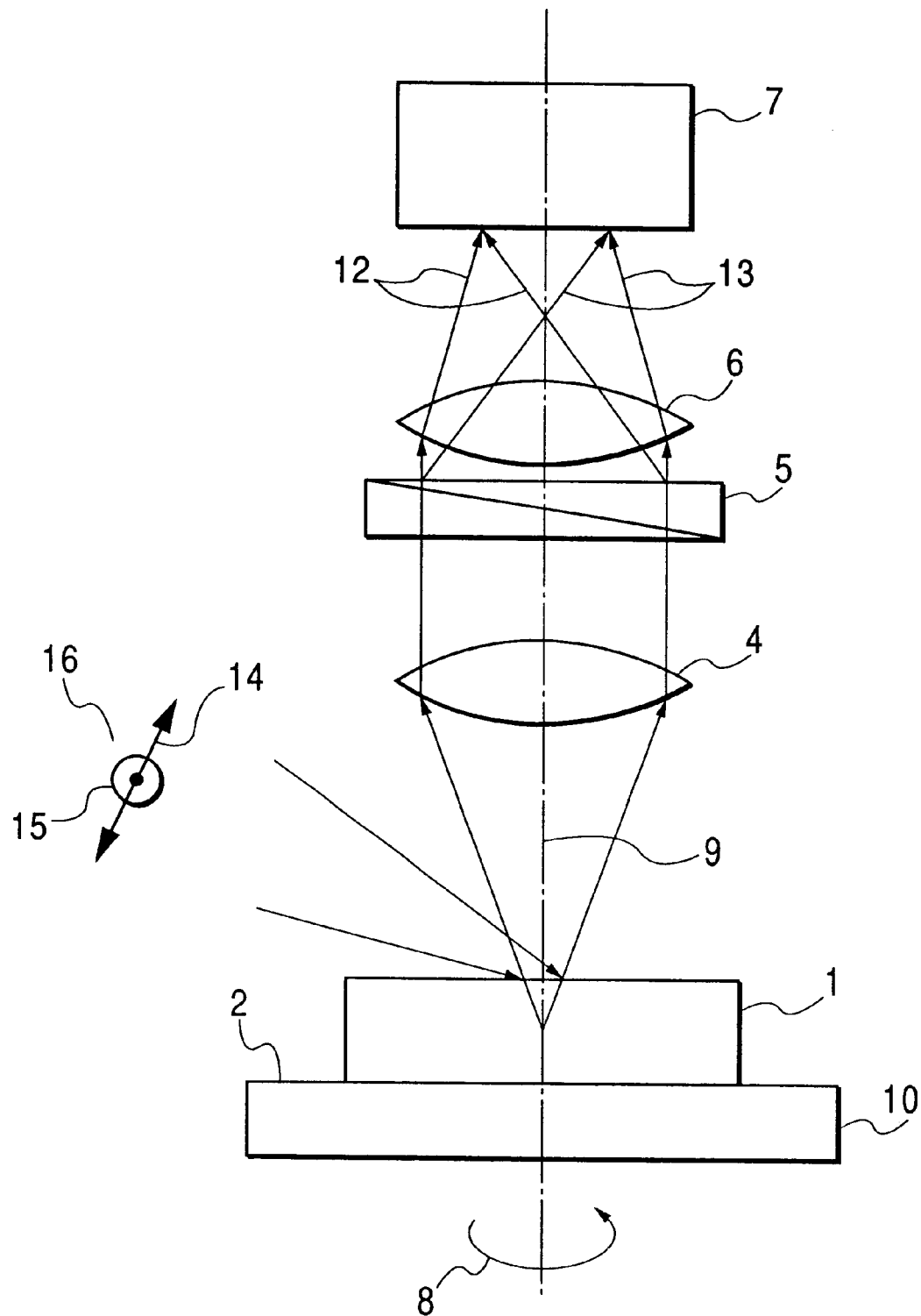
FIG. 4 is a view showing the arrangement of the third embodiment.

The third embodiment will be described next with reference to FIG. 4.

This apparatus comprises a laser irradiation unit (not shown) for obliquely irradiating a laser beam onto the observation surface of an object, a polarizer (not shown) for polarizing the laser beam to irradiate light 16 containing a p-polarized light component 14 and an s-polarized light component 15 at a predetermined ratio onto the object, an objective lens 4 used to observe scattered light generated by a defect in the object or on the surface of the object upon incidence of the laser beam, a polarizer 5 for polarizing the scattered light from the object to extract a p-polarized light component 12 or an s-polarized light component 13, an imaging lens 6, a light-receiving element 7, and a rotating mechanism 8 for rotating an object 1 to change the incident direction of the laser beam on the object 1. The rotating mechanism 8 comprises a stage 10 capable of rotating the object about an observation optical axis 9. The incident direction of the laser beam on the object 1 can be arbitrarily selected by rotating the stage 10. The object 1 can also be moved on the plane of the stage 10 such that the entire surface of the object 1 can be measured. The incident angle is set such that the direction of the light reflected by the object 1 does not coincide with the observation optical axis 9.

In this arrangement, the laser beam containing various polarized light components is polarized to obtain light containing a p-polarized light component and an s-polarized light component at a predetermined ratio by the polarizer, and this light is irradiated on the object 1. As described above in the first and second embodiments, when light containing a p-polarized light component and an s-polarized light component is irradiated on the object, the p-polarized light component is transmitted through the observation surface 2 almost without being influenced by scattering due to unevenness on the observation surface 2, and becomes refracted light. The light to be observed contains, as a major component, scattered light of the p-polarized light component due to a defect or the like in the object 1, and also partially contains an s-polarized light component due to unevenness on the observation surface 2. The s-polarized light component is reflected by the unevenness on the observation surface and observed through the light-receiving element as an s-polarized light component.

However, when p-polarized light component and s-polarized light component of the laser beam to be irradiated on the object are mixed at a predetermined ratio, scattering and reflection occur based on a principle different from that is mentioned above. Such a phenomenon is also observed at a specific laser beam incident angle. With this arrangement, more specific shape information of a defect in the object or on the surface of the object can be obtained.

To suppress the influence of dependence of the incident laser beam on azimuth due to poor mechanical accuracy of the rotating mechanism (including flatness of the stage), the number of incident directions is preferably as large as possible. In this embodiment, the laser beam to be irradiated on the object is a parallel beam. However, a condensed beam may be used. In addition, Wollaston prisms may be used in place of the polarizers.

In this embodiment, the laser beam is irradiated from a plurality of directions by rotating the object. Instead, the object may be fixed while the laser beam irradiation means is rotated about the observation optical axis. In this case, a means for rotating the polarizer between the objective lens and the imaging lens in accordance with rotation of the laser irradiation means is provided.

According to the third embodiment, defects or the like in the object can be separated from those on the surface. In addition, as in the first and second embodiments, the shape information of a defect or the like in the object or on the surface of the object can be obtained.

Figure 5:
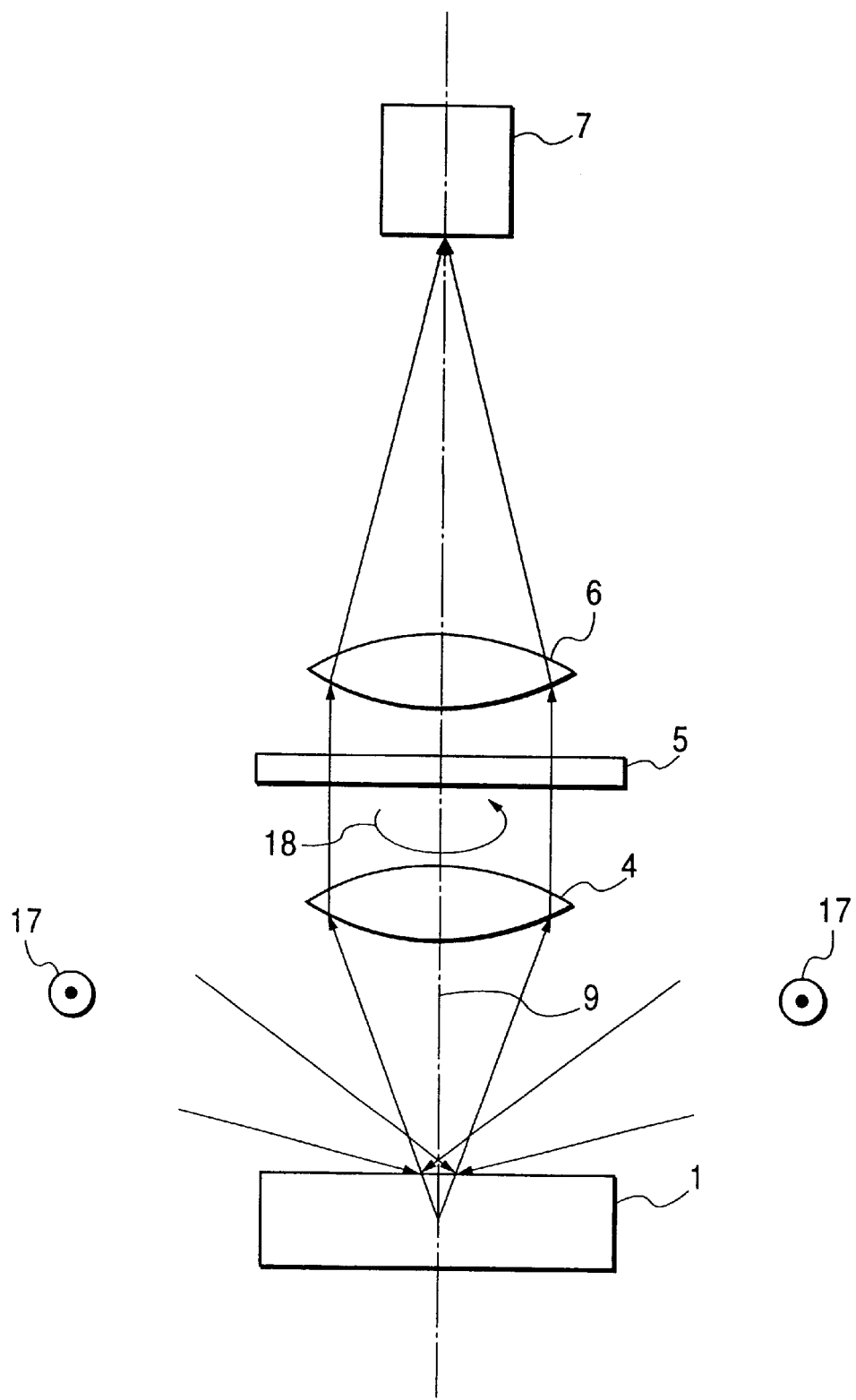
FIG. 5 is a view showing the arrangement of the fourth embodiment.

The fourth embodiment will be described with reference to FIG. 5.

The apparatus of this embodiment comprises a plurality of laser irradiation units (not shown) for obliquely irradiating laser beams onto the observation surface of an object, polarizers (not shown) for respectively polarizing the laser beams to irradiate light 17 containing an s-polarized light component onto the object, an objective lens 4 used to observe scattered light generated by unevenness on the surface of the object upon incidence of the laser beam, a polarizer 5 for polarizing the scattered light from the object to extract a polarized light component in a predetermined direction, a polarizer rotating mechanism 18 for rotating the polarizers in accordance with the positions of the laser irradiation means for irradiating the laser beams onto the object, an imaging lens 6, and a light-receiving element 7.

The plurality of laser irradiation units are placed around an observation optical axis 9 while being separated from the observation optical axis 9 by an equal distance. The each of angles formed by the observation optical axis 9 and the laser irradiation units as to the laser irradiation units is equal respectively.

To suppress the influence of dependence of the incident laser beam on azimuth, the number of incident directions is preferably as large as possible. In this embodiment, the laser beam to be irradiated on the object is a parallel beam. However, a condensed beam may be used. In addition, Wollaston prisms may be used in place of the polarizers.

In this arrangement, the laser beam containing various polarized light components is polarized to obtain light 17 containing an s-polarized light component, and the light 17 is irradiated on the object 1. The laser irradiation means sequentially irradiates the laser beam with time lags. The polarizer 5 is rotated by the polarizer rotating mechanism 18 to an appropriate angle in accordance with the position of the laser irradiation means. Since the irradiated laser beam is an s-polarized light component, the incident light is mostly reflected by the observation surface 2 and rarely transmitted through the observation surface 2. The incident angle is set such that the direction of the light reflected by the object does not coincide with the observation optical axis 9. With this arrangement, when the incident light generates scattered light by unevenness on the observation surface of the object, and the scattered light is observed.

With this arrangement, as laser beams can be continuously irradiated, laser irradiation on the object from a plurality of incident directions can be performed in a short time. In addition, the laser beam irradiation angle can be changed while keeping the object and the laser irradiation means fixed in position. Therefore, measurement can be stably performed.

The laser beams irradiated on the object by the laser irradiation means may have different wavelengths. In this case, the light-receiving element is imparted wavelength selectivity. With this arrangement, measurement can be performed at a higher speed.

In this embodiment, an s-polarized light component is irradiated on the object. However, a p-polarized light component may be irradiated on the object, as in the second embodiment. Alternatively, as in the third embodiment, light containing both a p-polarized light component and an s-polarized light component may be irradiated on the object. In these cases, both the effect of the fourth embodiment and that of the second or third embodiment can be obtained.

As has been described above, according to the present invention, shape information of a defect in the object or on the surface of the object can be obtained. When a plurality of defects form a composite defect or are close to each other, the composite defect or close state of the defects can be measured by measuring scattered light from the object.

As described above, according to the present invention, the defect evaluation apparatus can separate defects or foreign substances in an object and inspect the defect anisotropy.

When the scattering intensity from the object is plotted with respect to the laser beam incident direction, i.e., azimuth, the shape of a defect in the object or on the surface of the object can be specified on the basis of a change in scattering intensity.

Since laser beams can be simultaneously irradiated on the object from a plurality of directions, and the resulting scattered light can be measured, the measurement time can be shortened.

What is claimed is:

1. A defect evaluation apparatus comprising:

laser irradiation means for obliquely irradiating a laser beam onto an object; and observation means for observing scattered light from inside the object or a surface of the object, wherein said laser irradiation means irradiates the laser beam containing a p-polarized light component and an s-polarized light component at a predetermined ratio onto the object from a plurality of incident directions around an observation optical axis, and said observation means receives the scattered light from the object to obtain shape information of a defect or the like in the object and/or on the surface of the object while separating the shape information of the defect or the like in the object from the shape information of the defect or the like on the surface of the object.

2. An apparatus according to claim 1, wherein the laser beam irradiated on the object is light containing a p-polarized light component, and the shape information of the defect in the object is obtained while separating the shape information of the defect or the like in the object from the shape information of the defect or the like on the surface of the object.

3. An apparatus according to claim 1, wherein the laser beam irradiated on the object is light containing an s-polarized light component, and the shape information of the defect on the surface of the object is obtained while separating the shape information of the defect or the like on the surface of the object from the shape information of the defect or the like in the object.

4. An apparatus according to claim 1, wherein the defect is one of a defect, a foreign substance, a flaw, a particle, and unevenness.

5. An apparatus according to claim 1, wherein the laser beam is irradiated on the object from the plurality of incident directions around the observation optical axis by rotating the object about the observation optical axis.

6. An apparatus according to claim 1, wherein the laser beam is irradiated on the object from the plurality of incident directions around the observation optical axis by rotating said laser irradiation means about the observation optical axis.

7. An apparatus according to claim 1, wherein laser beams are irradiated on the object from a plurality of incident directions around the observation optical axis by a plurality of laser irradiation means.

8. An apparatus according to claim 7, wherein the laser beam irradiated from said plurality of laser irradiation means have different wavelengths.

9. A defect evaluation method comprising:
 the laser irradiation step of obliquely irradiating a laser beam onto an object; and
 the observation step of observing scattered light from inside the object or a surface of the object,
 wherein the laser beam containing a p-polarized light component and an s-polarized light component at a predetermined ratio irradiated onto the object from a plurality of incident directions around an observation optical axis, thereby obtaining shape information of a defect in the object or on the surface of the object while separating the shape information of the defect or the like in the object from the shape information of the defect or the like on the surface of the object.

* * * * *